US011484731B2

(12) United States Patent
Deligianni et al.

(10) Patent No.: US 11,484,731 B2
(45) Date of Patent: Nov. 1, 2022

(54) COGNITIVE OPTOGENETICS PROBE AND ANALYSIS

(71) Applicant: INTERNATIONAL BUSINESS MACHINES CORPORATION, Armonk, NY (US)

(72) Inventors: Hariklia Deligianni, Alpine, NJ (US); Ko-Tao Lee, Yorktown Heights, NY (US); Ning Li, White Plains, NY (US); Devendra Sadana, Pleasantville, NY (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 712 days.

(21) Appl. No.: 15/808,122

(22) Filed: Nov. 9, 2017

(65) Prior Publication Data

US 2019/0134420 A1 May 9, 2019

(51) Int. Cl.
*A61N 5/06* (2006.01)
*G16H 40/63* (2018.01)
(Continued)

(52) U.S. Cl.
CPC ........... *A61N 5/062* (2013.01); *A61N 5/0601* (2013.01); *B82Y 5/00* (2013.01); *G01J 3/44* (2013.01);
(Continued)

(58) Field of Classification Search
CPC .................................................. A61N 5/0622
See application file for complete search history.

(56) References Cited

U.S. PATENT DOCUMENTS 6,614,523 B1 * 9/2003 Boss ................ G01N 33/54373
356/301
7,729,773 B2 * 6/2010 Sloan ................... A61N 1/36082
607/45
(Continued)

FOREIGN PATENT DOCUMENTS

CN 102088906 A 6/2011
CN 104548383 A 4/2015
(Continued)

OTHER PUBLICATIONS

Kim, Min Hyuck, et al. "Probe-pin device for optical neurotransmitter sensing in the brain." Nanosensors, Biosensors, and Info-Tech Sensors and Systems 2015. vol. 9434. International Society for Optics and Photonics, 2015. (Year: 2015).*
(Continued)

*Primary Examiner* — Carl H Layno
*Assistant Examiner* — Manolis Pahakis
(74) *Attorney, Agent, or Firm* — Cantor Colburn LLP; Stosch Sabo (57) ABSTRACT

Technical solutions are described for implementing an optogenetics treatment using a probe and probe controller are described. A probe controller controls a probe to perform the method that includes emitting, by a light source of the probe, the probe is embeddable in a tissue, a light wave to interact with a corresponding chemical in one or more cells in the tissue. The method further includes capturing, by a sensor of the probe, a spectroscopy of the light wave interacting with the corresponding chemical. The method further includes sending, by the probe, the spectroscopy to an analysis system. The method further includes receiving, by the probe, from the analysis system, adjusted parameters for the light source, and adjusting, by a controller of the probe, settings of the light source according to the received adjusted param-
(Continued)

eters to emit a different light wave to interact with the corresponding chemical.

23 Claims, 5 Drawing Sheets (51) Int. Cl.
  B82Y 5/00 (2011.01)
  G01J 3/44 (2006.01)
  G01N 21/65 (2006.01)
  G06N 20/00 (2019.01)
(52) U.S. Cl.
  CPC .......... *G01N 21/658* (2013.01); *G06N 20/00* (2019.01); *G16H 40/63* (2018.01); *A61N 2005/0612* (2013.01); *A61N 2005/0626* (2013.01); *A61N 2005/0651* (2013.01); *G06T 2207/20081* (2013.01)

(56) References Cited

U.S. PATENT DOCUMENTS

| | | | | |
|---|---|---|---|---|
| 8,934,965 | B2* | 1/2015 | Rogers | A61B 5/0036 600/545 |
| 9,907,496 | B1* | 3/2018 | Okandan | A61B 5/1459 |
| 9,993,661 | B2* | 6/2018 | Bourke, Jr. | A61N 5/062 |
| 10,001,442 | B2* | 6/2018 | Xie | G01N 21/658 |
| 10,376,600 | B2* | 8/2019 | Peyman | A61K 47/6923 |
| 10,384,071 | B2 | 8/2019 | Vo-Dinh et al. | |
| 10,391,330 | B2* | 8/2019 | Bourke, Jr. | A61P 13/08 |
| 10,576,268 | B2* | 3/2020 | Cao | A61B 5/4094 |
| 10,694,951 | B2* | 6/2020 | Kinser | A61B 5/0075 |
| 2009/0054955 | A1 | 2/2009 | Kopell et al. | |
| 2010/0016783 | A1 | 1/2010 | Bourke, Jr. et al. | |
| 2010/0105098 | A1 | 4/2010 | Frederiske et al. | |
| 2010/0292931 | A1* | 11/2010 | Wang | G01N 21/6458 702/19 |
| 2012/0143043 | A1* | 6/2012 | Peyman | A61K 41/0028 600/407 |
| 2013/0224756 | A1* | 8/2013 | Cohen | C07K 14/00 435/6.17 |
| 2013/0331036 | A1* | 12/2013 | Baker | A61B 5/14542 455/41.3 |
| 2014/0155733 | A1* | 6/2014 | Peyman | G01R 33/285 600/417 |
| 2014/0364743 | A1 | 12/2014 | Godavarty et al. | |
| 2015/0157713 | A1* | 6/2015 | Peyman | A61K 47/6929 600/407 |
| 2016/0004298 | A1 | 1/2016 | Mazed et al. | |
| 2016/0022976 | A1* | 1/2016 | Peyman | A61K 47/6929 600/407 |
| 2016/0030765 | A1 | 2/2016 | Towne et al. | |
| 2016/0151671 | A1* | 6/2016 | Weast | A63B 24/0075 434/247 |
| 2016/0178618 | A1 | 6/2016 | Freyer et al. | |
| 2017/0143985 | A1* | 5/2017 | Degenaar | A61N 5/0601 |
| 2017/0228508 | A1* | 8/2017 | Cook | G16H 40/63 |
| 2017/0316487 | A1* | 11/2017 | Mazed | G06Q 30/0241 |
| 2017/0356851 | A1* | 12/2017 | Kinser | G01N 21/658 |
| 2018/0093092 | A1* | 4/2018 | Howard | G01N 27/4145 |
| 2018/0103847 | A1* | 4/2018 | Kinser | A61B 5/0084 |
| 2018/0103848 | A1* | 4/2018 | Kinser | A61N 5/0622 |
| 2018/0193663 | A1* | 7/2018 | Deligianni | A61B 5/24 |
| 2018/0270474 | A1* | 9/2018 | Liu | A61B 6/508 |
| 2018/0364192 | A1* | 12/2018 | Cao | A61B 5/1468 |
| 2019/0101504 | A1* | 4/2019 | Deligianni | G01N 27/48 |
| 2019/0314628 | A1* | 10/2019 | Park | G01J 3/44 |
| 2020/0038680 | A1* | 2/2020 | Degenaar | A61N 5/0601 |
| 2020/0138296 | A1* | 5/2020 | Pisanello | A61B 5/0075 |
| 2020/0354660 | A1* | 11/2020 | Atzler | C12M 41/46 |
| 2022/0003676 | A1* | 1/2022 | Mazed | G06Q 20/321 |

FOREIGN PATENT DOCUMENTS

| | | |
|---|---|---|
| CN | 105828720 A | 8/2016 |
| CN | 107249460 A | 10/2017 |
| CN | 108634964 A | 10/2018 |
| EP | 1488002 A2 | 12/2004 |
| JP | 2012524795 A | 10/2012 |
| JP | 2017527419 A | 9/2017 |
| WO | 2005035791 A1 | 4/2005 |
| WO | 2010041231 A2 | 4/2010 |

OTHER PUBLICATIONS

International Search Report; International Application No. PCT/IB2018/058602; International Filing Date: Nov. 2, 2018; dated Feb. 15, 2019; 9 pages.
Adamantidis et al., "Sleep and metabolism: shared circuits, new connections." Trends in Endocrinology & Metabolism 19.10, 2008, p. 362-370.
International Search Report; International Application No. GB2007216.1; International Filing Date: Nov. 2, 2018; dated Jun. 25, 2021; 4 pages.
International Search Report; International Application No. 201880071187.0; International Filing Date: Nov. 9, 2017; dated Apr. 23, 2021; 9 pages.
JP Office Action (English Translation); dated Jan. 24, 2022, Application No. 2020-522961; Filed: Nov. 2, 2018; 3 pages.

* cited by examiner

COGNITIVE OPTOGENETICS PROBE AND ANALYSIS

BACKGROUND

The present invention relates in general to optogenetics and more specifically, to using optogenetics and cognitive computing to monitor optogenetics treatment results and adjust the treatment using a feedback loop.

Optogenetics is a technique that allows for deep insight in fields such as neuroscience and neuropathology and has been used to study the roles of various neurons and cells in disease states such as Parkinson's, epilepsy, and depression. Typically, optogenetics treatment uses scopes that may be invasive. There is a need to improve optogenetics for deeper and non-invasive applications.

SUMMARY

Embodiments of the present invention are directed to an optogenetics treatment using a probe and probe controller.

One or more embodiments of an example computer-implemented method for implementing an optogenetics treatment using a probe and probe controller are described. The probe controller controls the probe to perform the method that includes emitting, by a light source of the probe, wherein the probe is embeddable in a tissue, a light wave to interact with a corresponding chemical in one or more cells in the tissue. The method further includes capturing, by a sensor of the probe, a spectroscopy of the light wave interacting with the corresponding chemical. The method further includes sending, by the probe, the spectroscopy to an analysis system. The method further includes receiving, by the probe, from the analysis system, adjusted parameters for the light source. The method further includes adjusting, by a controller of the probe, settings of the light source according to the received adjusted parameters to emit a different light wave to interact with the corresponding chemical.

Further, one or more embodiments are described of a system that includes a probe that performs optogenetics treatment. The probe includes a light source, a sensor, and a controller. The system further includes an analysis system that wirelessly communicates with the probe, to automatically optimize the optogenetics treatment. The automatic optimization includes emitting, by the light source of the probe that is embeddable in a tissue, a light wave to interact with a corresponding chemical in one or more cells in the tissue. The optimization further includes capturing, by the sensor of the probe, a spectroscopy of the light wave interacting with the corresponding chemical. The optimization further includes sending, by the probe, the spectroscopy to an analysis system. The optimization further includes receiving, by the probe, from the analysis system, adjusted parameters for the light source. The optimization further includes adjusting, by the controller of the probe, settings of the light source according to the received adjusted parameters to emit a different light wave to interact with the corresponding chemical.

Further, according to one or more embodiments described a computer program product includes a computer readable storage medium having program instructions embodied therewith. The program instructions are executable by a processing circuit to cause the processing circuit to automatically optimize an optogenetics treatment. The automatic optimization includes emitting, by the light source of the probe that is embeddable in a tissue, a light wave to interact with a corresponding chemical in one or more cells in the tissue. The optimization further includes capturing, by the sensor of the probe, a spectroscopy of the light wave interacting with the corresponding chemical. The optimization further includes sending, by the probe, the spectroscopy to an analysis system. The optimization further includes receiving, by the probe, from the analysis system, adjusted parameters for the light source. The optimization further includes adjusting, by the controller of the probe, settings of the light source according to the received adjusted parameters to emit a different light wave to interact with the corresponding chemical.

Further, one or more embodiments are described of a probe that is embeddable in a patient, the probe performs an optogenetics treatment for the patient. The probe includes a light source that emits a light wave to interact with a corresponding chemical in one or more cells in a tissue in which the probe is embeddable. The probe further includes a sensor that captures a spectroscopy of the light wave interacting with the corresponding chemical. The probe further includes a controller that sends the captured spectroscopy to an analysis system wirelessly. The controller further receives, in response, from the analysis system, adjusted parameters for the light source. The controller further adjusts settings of the light source according to the received adjusted parameters to emit a different light wave to interact with the corresponding chemical.

Further, one or more embodiments are described of an analysis system that automatically adjusts an optogenetics treatment for a patient. The analysis system includes a memory, and a processor coupled with the memory. The processor receives captured spectroscopy sent wirelessly by a probe that is embeddable within the patient, the spectroscopy captured by a light sensor of the probe in response to emission of a light wave by a light source of the probe, the light wave being emitted to activate one or more cells of the patient. The processor further compares the captured spectroscopy with a predetermined spectroscopy. The processor further determines an updated set of parameters for the light source of the probe in response to the captured spectroscopy not matching the predetermined spectroscopy. The processor further sends the updated set of parameters to the probe to cause the light sensor to generate a different emission to activate the cells.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Described herein are technical solutions for using optogenetics and cognitive computing to monitor optogenetics treatment results and adjust the treatment using a feedback loop. For example, the technical solutions described herein include optogenetics treatment systems that include a probe, a surface enhanced Raman sensor, a communication device, and a computing device that analyzes the output of the sensor and adjusts the configuration of the probe according to the analysis. The output of the sensor indicates effects of light waves emitted by the probe on one or more cells of a patient being treated by the optogenetics system. Based at least in part on the above-described analysis of the output of the sensor, the computing device determines that a desired effect is being observed, and if not, adjusts the configuration of the probe, such as by adjusting one or more parameters of the probe, such as those that change the light wave being emitted by the probe. Thus, the probe uses a different light wave for further treatment. In one or more examples, the probe may emit one or more light waves, and the adjustment may change any one or more of the light waves. Thus, the technical solutions described herein facilitate improving an optogenetics system and the use thereof for treating patients seeking treatments for chronic pain, depression, Parkinson's disease, addiction, and the like.

Optogenetics is an established technique that uses light to modulate membrane voltage in cells, such as neural cells, in body tissue. The light can be used to trigger changes in proteins that modulate membrane potentials in the cells through excitatory or inhibitory membrane currents. This ability to modulate cells has proven instrumental in preclinical studies and holds enormous potential for the treatment of diseases such as Parkinson's, epilepsy, chronic pain, addiction, and depression, among others. However, current techniques used for optogenetics control are too invasive for clinical applications. That is, although optogenetics allows researchers to study parts of the body like never before, it is limited because it is invasive, and further, light, particularly visible light, cannot travel very deeply into tissue. Further, a technical challenge with optogenetics systems is the lack of configurability of the light waves used for the treatment on an individual basis. Additionally, optogenetics solutions typically suffer from Joule heating because of high energy light sources, and also lack a feedback loop for cognitive training.

The subject invention addresses such technical challenges and others by providing novel and advantageous methods and systems for performing optogenetics using a probe with low power light source, a surface enhanced Raman spectroscopy sensor, a computing device receiving the Raman spectroscopy to examine the optogenetics results. The technical solutions described herein, based on the use of low power light sources facilitate lowering the power consumption and heating, which further allows putting more light sources close to cells and neurons. Further, the use of Raman spectroscopy to collect information around the cells facilitates forming a cognitive study loop. In one or more examples, the technical solutions described herein learn cognitively an optimal treatment for the patient through the analytics of the surface enhanced Raman spectroscopy (SERS) feedback system, optimize the parameters to apply to the light sources to improve the treatment results. The technical solutions thus learn to adjust the therapy being conducted using the optogenetics system.

Thus, the typical solutions have a technical challenge of treating a patient using optogenetics with low powered light sources using a probe embedded in a patient body and adjusting the treatment automatically according to individual results. The technical solutions described herein address the technical challenge described above by using light emitting diode (LED) based light sources in a probe that is embedded in the patient body and controlling the parameters of the light sources by analyzing spectroscopy results from a sensor of the probe. Thus, the technical solutions described herein address the technical challenges described earlier.

Figure 1:
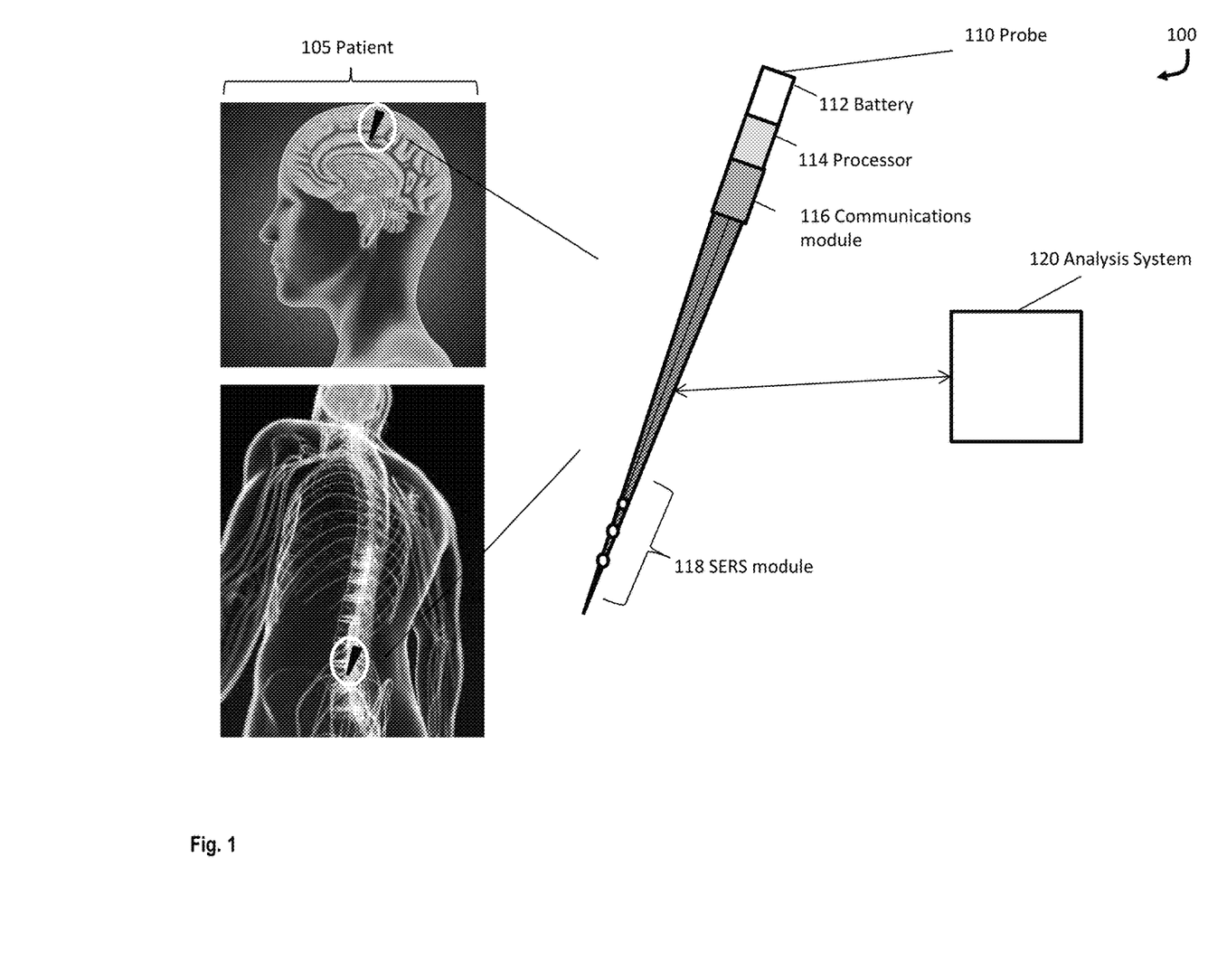
FIG. 1 depicts a pictorial representation of an example optogenetics system according to one or more embodiments of the present invention.
Figure 2:
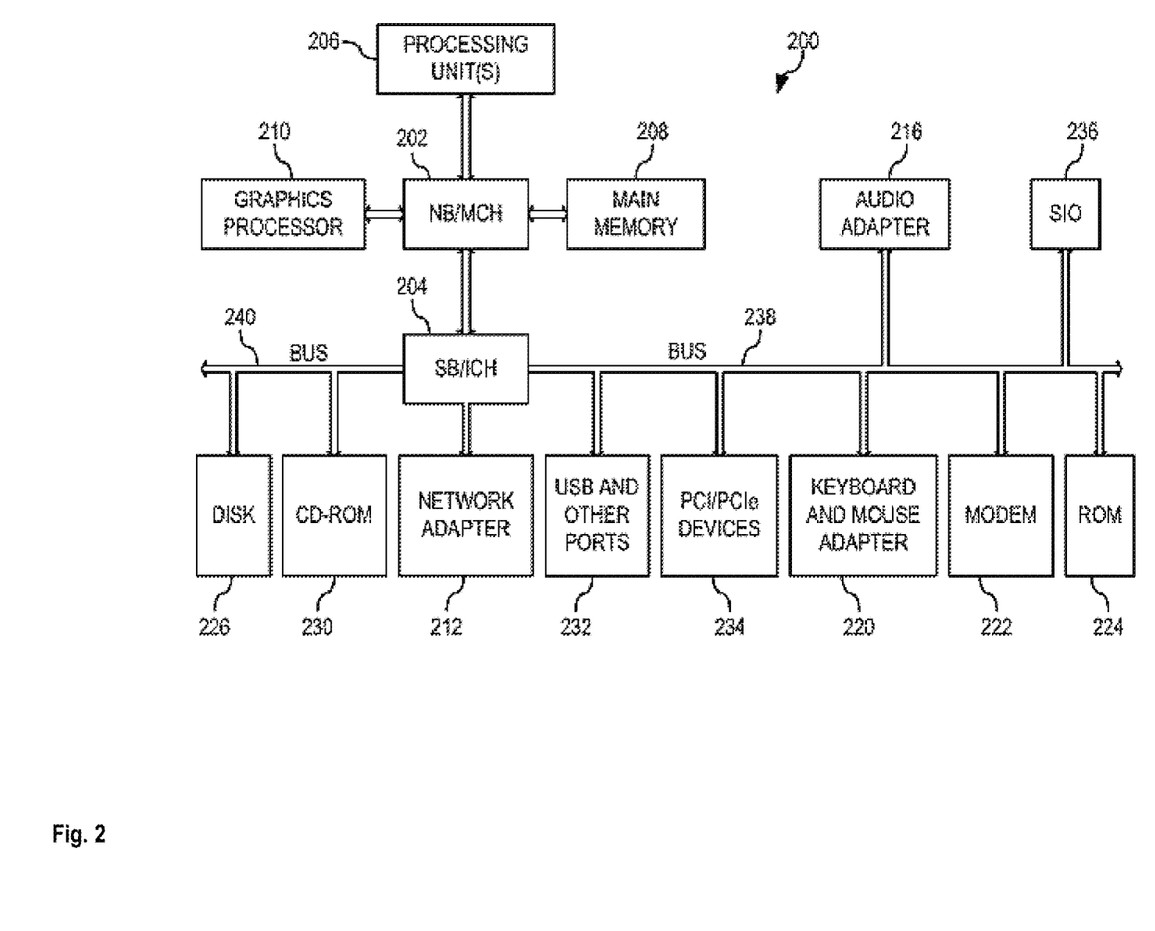
FIG. 2 is a block diagram of an example data processing system according to one or more embodiments of the present invention.
Figure 3:
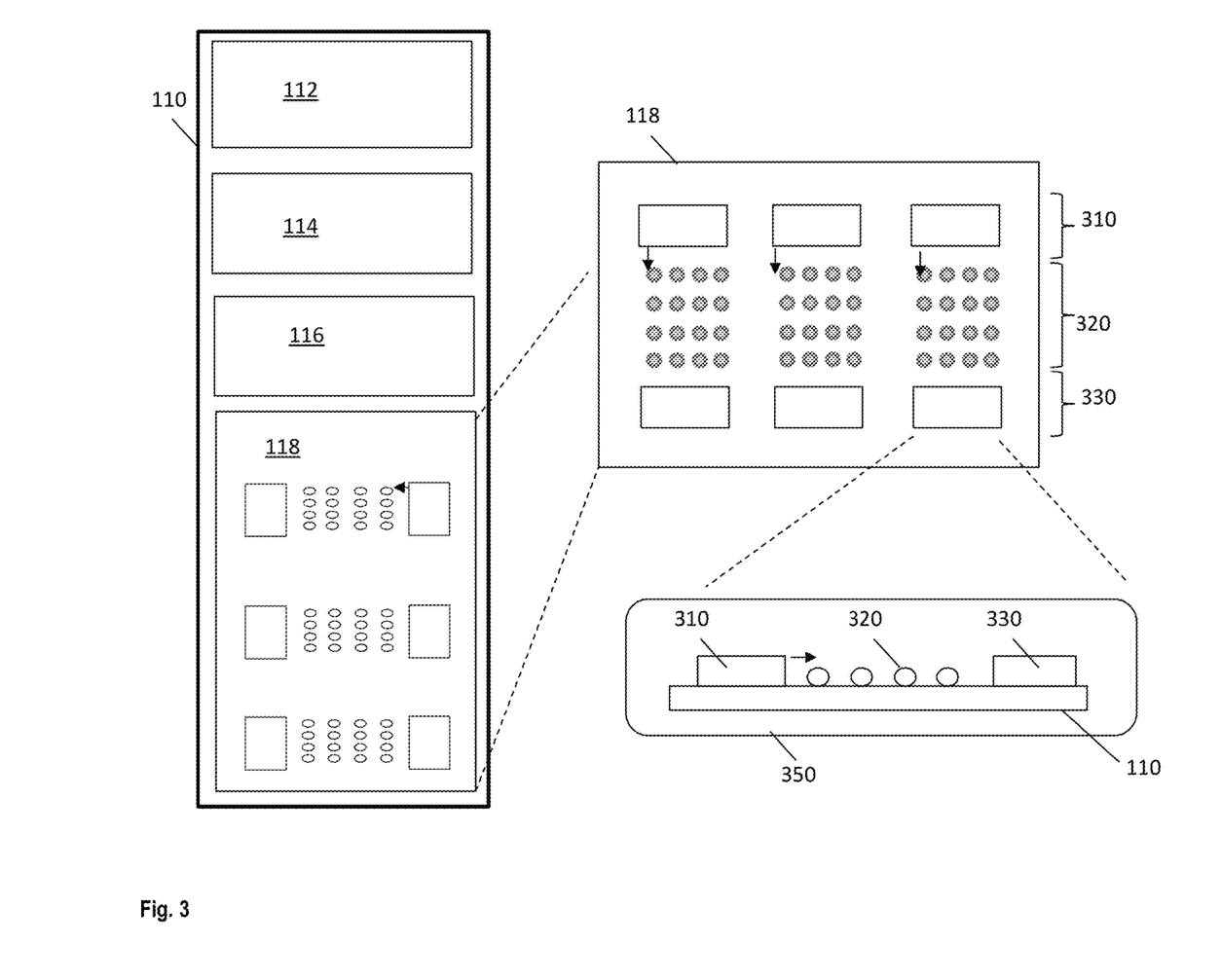
FIG. 3 illustrates an example probe according to one or more embodiments of the present invention.

It should be noted that the illustrative embodiments of the technical solutions described herein may be utilized in many different types of data processing environments. In order to provide a context for the description of the specific elements and functionality of the illustrative embodiments, FIGS. 1, 2, and 3 are provided hereafter as examples in which aspects of the illustrative embodiments may be implemented. It should be appreciated that FIGS. 1, 2, and 3 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example optogenetics system according to one or more embodiments of the present invention. The system 100 is being used to treat a patient 105. The system includes a probe 110 and an analysis system 120 among other components. As depicted the probe 110 is embedded in the patient 105. It should be noted that the probe 110 may be embedded in a different location in the patent 105 than the examples depicted in the FIG. 1. Further, it should be noted that although the patient 105 depicted in the examples in FIG. 1 is a human, the technical solutions described herein may be used for treating other patients, such as animals.

The probe 110 includes components such as a battery 112, a processor 114, a communications module 116, and a SERS module 118, among others. The battery 112 powers the other components of the probe 110. The processor 114 is responsible for the operations of the probe 110. The processor 114 may be a microprocessor, or any other type of processor that facilitates execution of one or more computer executable instructions. The processor 114 includes or is associated with a memory to read/store data.

The communications module 116 facilitates communication with the analysis system 120. In one or more examples, the communication may be wireless communication using a predetermined protocol. The communication may include sending to the analysis system 120 one or more captured spectroscopy results by the SERS module 118. The communication may further include receiving from the analysis system 120 one or more settings for adjusting the operation of the SERS module 118. In one or more examples, the communications module 116 includes a radio frequency (RF) coil for wireless communication & charging the battery 112.

The SERS module 118 includes one or more light sources. In one or more examples, the light sources are LEDs. The light sources emit light waves that are used for optogenetics. Further, the SERS module 118 includes a sensor that captures the SERS spectroscopy resulting from the light waves. In one or more examples, the processor 114 operates one or more electronic circuits to drive the light sources and collect SERS signal from the sensor of the SERS module 118.

The analysis system 120 receives the spectroscopy captured by the sensor(s) and analyzes the data. The analysis system 120 uses data analytics, such as machine learning using cognitive computing and optimizes the treatment being used for the patient 105. The optimization includes adjusting the light waves being emitted by the light sources. The analysis system 120 provides updated parameter values to use to the probe 110 that is embedded in the patient 105. The SERs module 118 is adjusted accordingly. Such a feedback from the analysis system continues at a predetermined frequency or on an on-demand basis to automatically improve the treatment of the patient 105.

In one or more examples, the analysis system 120 is a computing device, such as portable computing device (smartphone, digital assistant, a tablet computer, a laptop computer, etc.), a server computer, a desktop computer, or any other such computing device.

FIG. 2 is a block diagram of an example data processing system according to one or more embodiments of the present invention. Data processing system 200 is an example of a computer, such as the analysis system 120 in FIG. 1, in which computer usable code or instructions implementing the processes for illustrative embodiments of the present invention may be located.

In the depicted example, data processing system 200 employs a hub architecture including north-bridge and memory controller hub (NB/MCH) 202 and south-bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®, or the like. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 illustrates an example probe according to one or more embodiments of the present invention. The probe 110 is shown with the one or more components described earlier including the battery 112, the processor 114, the communication module 116, and the SERS module 118. The probe 110 is embedded within the patient 105 in a tissue 350, where cells 320 (and/or neurons) from the tissue 350 are to be treated using optogenetics.

The SERS module 118 includes one or more light sources, such as single wavelength LEDs 310. The light waves emitted by the light sources affect the cells 320 that are adjacent to the light source 310, and in the direction of the light waves emitted. The SERS module 118 further includes one or more sensors 330, each sensor 330 corresponding to a respective light source 310. The sensor 330 captures the spectroscopy of the light waves interacting with the cells 320. The sensors 330 are placed at a predetermined distance from the light sources 310 in the direction of the emission of the light waves (see arrow), as depicted in FIG. 3. As is depicted, because the light sources used are LEDs that consume power less than a predetermined threshold, the heat generated to emit the light waves by the light sources 310 does not harm the tissue 305. Further, this facilitates the SERS module 118 to include multiple light sources 310, each light source emitting a different light wave.

For example, the light waves emitted may differ in wavelength, pulse width, total number of waves sent per unit time (for example per day), pulse repetition frequency (PRF) (for example pulses per second), and time at which light wave is emitted, among other attributes and a combination thereof. The controller 114 stores the parameter configuration for each light source 310 and instructs the light sources 310 to emit the light waves accordingly. The parameter configuration is determined based on a condition that is being treated using the probe 110. For example, the different configurations may treat different conditions such as chronic pain, depression, Parkinson's disease, addiction, and the like.

Because different tissue 305 can react differently to a given light wave, the effect of a light wave on a first patient 105 may be different from the effect of the light wave on a second patient 105. The effect of the light wave on the cells 320 can be monitored using the spectroscopy captured by the sensors 330. The spectroscopy facilitates analysis of chemical concentrations in the cells 320 and the effect on the chemicals because of the light waves emitted by the light sources 310.

Accordingly, the sensors 330 capture and send the spectroscopy to the analysis system 120 for determining the effect of the light waves on the cells 320, and as such the patient 105. The spectroscopy is sent using the communications module 116. In one or more examples, the controller 112 is notified once the spectroscopy has been captured, and in response the controller 112 instructs the communication module 116 to forward the spectroscopy to the analysis system 120. In one or more examples, the spectroscopy is sent in real-time, for example as streaming data. Alternatively, or in addition, depending on the proximity of the analysis system 120 and the probe 110, the controller 114 stores the spectroscopy, for example as files, along with metadata associated with the spectroscopy. For example, if the analysis system 120 is a portable computer device, it may be moved outside a predetermined range in which the probe 110 is able to communicate, for example using RF communication, near field communication (NFC), or any other short range communication protocols. Once the analysis system 120 is in communication range with the probe 110, the analysis system 120 may generate and send a notification to the probe 110 indicating that it is ready to receive any outstanding spectroscopy data. Alternatively, or in addition, the analysis system 120 may have a predetermined schedule at which it receives data from the probe 110. In yet other examples, the analysis system 120 sends a request to the probe 120 to send spectroscopy data, and in response the probe 110 sends spectroscopy data that has been stored since the last such transfer.

When the analysis system 120 comes into proximity with the probe 110, or when the analysis system 120 indicates that it is ready to receive the spectroscopy data, the controller 114 initiates the communications module 116 to forward the stored spectroscopy data and the corresponding metadata. In one or more examples, the metadata includes a timestamp when the spectroscopy was captured, when the light wave was emitted, the attributes of the light wave emitted, and the like.

The analysis system 120 analyzes the Raman spectroscopy data that is captured by the sensors 330. The analysis system 120 uses machine learning, such as neural networks, to optimize the parameter configuration of the light sources based on the results of the Raman spectroscopy. For example, the analysis system 120 compares the results of the analysis with predetermined thresholds that are indicative of expected results of the optogenetics treatment the patient 105 has undergone so far. For example, the results and the predetermined thresholds may include levels (or amounts) of adenosine, levels of channelrhodopsin proteins (ChR1, ChR2), levels of dopamine, serotonin, and other such chemicals and/or proteins in the cells 320, or a combination thereof. Using the machine learning algorithms, for example via application programming interface (API) of one or more service providers such as IBM™ WATSON™, GOOGLE PREDICTION API™, ALCHEMYAI™, and the like.

The analysis system 120, based on the findings of the machine learning, automatically configures the parameter configurations of the light sources 310 of the probe 110. In one or more examples, the analysis system 120 sends a new set of parameters to the probe 110 via the communications module 116. The controller 114, upon receiving the new set of parameters, updates the SERS module 118 accordingly, so that until further changes, light waves are emitted according to the updated parameters. Thus, the optogenetics treatment of the patient 105 is adjusted automatically by the optogenetics system 100.

Those of ordinary skill in the art will appreciate that the hardware in FIGS. 1, 2, and 3 may vary depending on the implementation. Other internal hardware or peripheral devices, such as flash memory, equivalent non-volatile memory, or optical disk drives and the like, may be used in addition to or in place of the hardware depicted in FIGS. 1, 2, and 3. Also, the processes of the illustrative embodiments may be applied to a multiprocessor data processing system, other than the SMP system mentioned previously, without departing from the spirit and scope of the present invention. Further, it should be noted that although Raman spectroscopy is described in the examples herein, in other examples, other type of spectroscopy may be captured and analyzed for automatically adjusting the optogenetics treatment.

Figure 4:
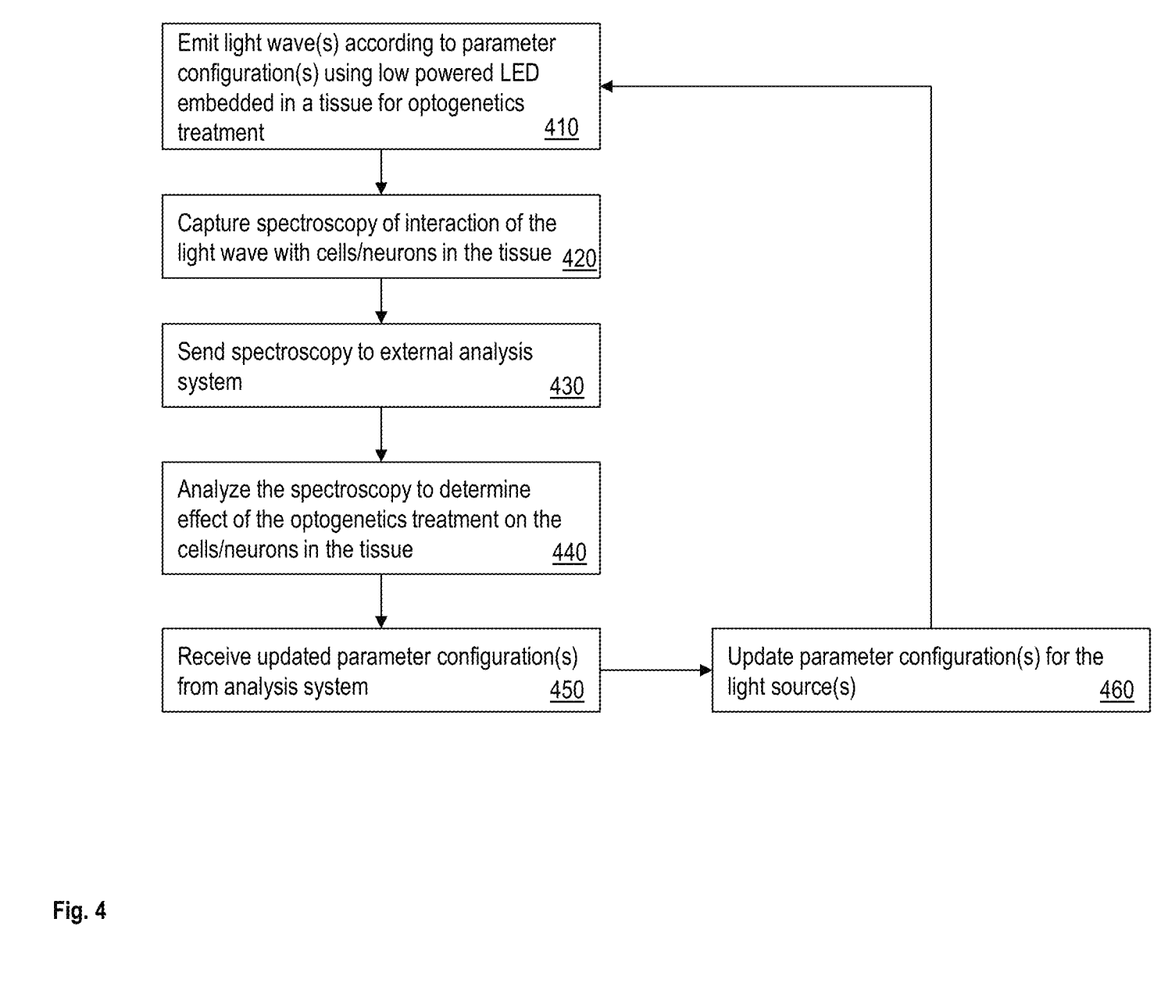
FIG. 4 is a flowchart outlining an example operation for performing and optimizing optogenetics treatment by adjusting an optogenetics probe according to one or more embodiments of the present invention.

FIG. 4 is a flowchart outlining an example operation for performing and optimizing optogenetics treatment by adjusting an optogenetics probe according to one or more embodiments of the present invention. The method includes emitting light waves according to parameter configurations using the low powered light sources 310, such as LEDs, that are embedded in the tissue 350 for optogenetics treatment, as shown at block 410. The light waves may be emitted by one or more of the light sources 310 according to a predetermined schedule. For example, a first parameter configuration for a first light source 310 determines a schedule at which the first light source 310 emits light waves, for example at a specific time(s) of day. The first parameter configuration further determines a wavelength of the light wave emitted by the first light source 310. Further, the first parameter configuration determines a pulse repetition frequency of the light wave. The first parameter configuration further determines a pulse width of each pulse in the light wave emitted by the first light source. The first parameter configuration further determines a number of pulses emitted in each instance of the light wave emitted. In one or more examples, a second parameter configuration for a second light source 310 is distinct from the first parameter configuration. Thus, the two light sources emit different types of light waves. In one or more examples, the two light sources 310 operate concurrently using their respective parameter configurations. Alternatively, the two light sources 310 operate on a sequential manner, for example the second light source emits light waves after the first light source has completed emission of light waves. The parameter configurations, in one or more examples, dictate the order in which the light sources 310 are operated. The light waves emitted activate one or more specific chemicals and/or proteins in the cells 320 within the tissue 350 and that are in proximity of the probe 110.

Further, the method includes capturing spectroscopy of interaction of the light wave(s) with the cells/neurons 320 in the tissue 350, as shown at block 420. The sensors 330 capture the spectroscopy, such as the Raman spectroscopy that is generated by single wave light sources. In one or more examples, the sensors 330 are configured to capture spectroscopy corresponding to specific chemicals and/or proteins in the tissue 350. For example, a first sensor 330 is configured to capture adenosine spectroscopy, a second sensor 330 is configured to capture dopamine spectroscopy, a third sensor 330 is configured to capture serotonin spectroscopy, and the like. Accordingly, the sensors 330 capture the predetermined light waves associated with the spectroscopy that each of the sensors 330 is configured to capture and monitor.

Further, the method includes sending the captured spectroscopy(ies) to the analysis system 120, as shown at block 430. As described herein, the captured spectroscopy data is transferred in real time, or at predetermined synchronization times, and/or based on proximity of the analysis system 120. The captured spectroscopy data is transferred wirelessly so that the probe 110 embedded in the patient does not have to be connected to a particular wire/device, thus enabling the patient 105 to move freely and not be inconvenienced for the data transfer. In one or more examples, the transfer of data, and the method of optimizing the treatment is performed completely transparently to the patient 105, without intervening the patient's 105 activities.

The method further includes, analyzing the spectroscopy data to determine effect of the optogenetics treatment on the cells/neurons 320 in the tissue 350, as shown at block 440. As described herein, the analysis includes using machine learning algorithms to compare the spectroscopy data from the probe 110 with predetermined results that are indicative of desired effects of the optogenetics treatment. Based on the difference between the predetermined results and the spectroscopy data from the probe 110, the analysis system 120, using the machine learning, determines adjustments for the light source parameters to change the light waves emitted by the light sources 310 to match the resulting spectroscopy with the predetermined results. The machine learning algorithms used by the analysis system 120 for refining the parameter configurations of the light sources 310 include regression algorithms, such as linear regression, logistic regression, multivariate adaptive regression splines (MARS), locally estimated scatterplot smoothing (LOESS), or any other regression based algorithms. Alternatively, or in addition, the machine learning algorithms include instance based learning such as k-nearest neighbors (kNN), learning vector quantization (LVQ), self-organizing map (SOM), and the like. Alternatively, or in addition, the machine learning may include using artificial neural network (ANN) based learning such as back-propagation, hopfield network, or any other ANN based learning. It should be noted that the above are just examples, and the in one or more examples, the analysis system 120 may use any other machine learning algorithm that is not listed here.

The method further includes the probe 110 receiving the updated parameter configuration(s) from analysis system 120, as shown at block 450. The updated parameter configurations are received via the communications module 116. Following which, the method includes updating the parameter configuration(s) for the light source(s) 310 by the controller 114, as shown at block 460. The method continues with the controller 114 using the updated parameter configurations to cause the light sources 310 to emit different light waves than before, and thus optimizing the optogenetics treatment for the patient 105. The parameter configurations may be further updated as described herein. Thus, the above method automatically optimizes the optogenetics treatment using a feedback loop to adjust the light waves emitted by the light sources of a probe embedded in the patient by changing the parameters of the light sources.

In one or more examples, the analysis system 120 sends the updated parameter configurations to a medical practitioner, such as a doctor, a nurse, or the like before sending the updated parameters to the probe 110. The analysis system 120 may send the updated parameters to the probe 110 only if approved by the medical practitioner. Alternatively, or in addition, the analysis system 120 ensures that the updated parameters are within predetermined parameters for the probe 110. In one or more examples, the predetermined parameters for the probe 110 are set by the medical practitioner so that the system operates automatically without the medical practitioner's intervention or approval as long as the updated parameters are within the predetermined range(s).

Figure 5:
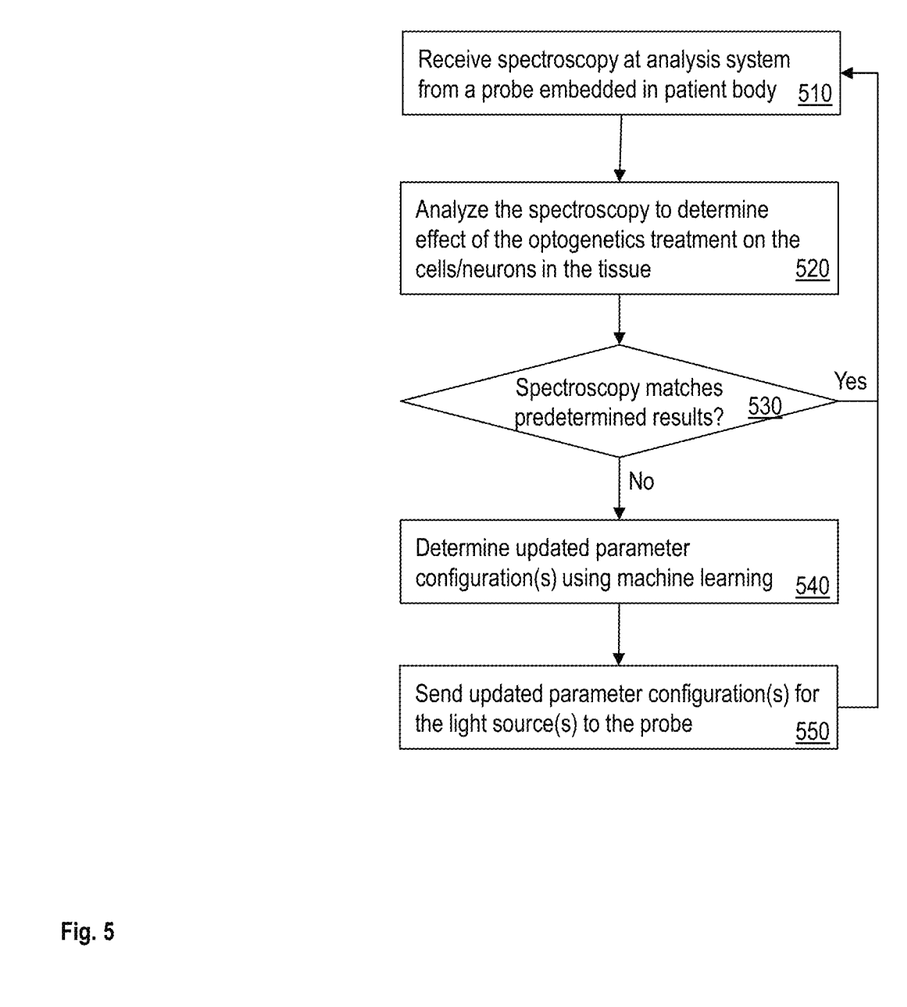
FIG. 5 illustrates a flowchart of an example method for optimizing an optogenetics treatment using a feedback loop according to one or more embodiments of the present invention.

FIG. 5 illustrates a flowchart of an example method for optimizing an optogenetics treatment using a feedback loop according to one or more embodiments of the present invention. The method includes receiving the spectroscopy by the analysis system 120 from the probe 110 that is embedded in the patient 105 body, as shown at block 510. As described herein, the spectroscopy data is captured by one or more sensors 330 of the probe 110 in response to light waves emitted by the corresponding light sources 310 of the probe 110. Further, the method includes analyzing the spectroscopy data to determine effect of the optogenetics treatment on the cells/neurons 320 in the tissue 350, as shown at block 520. The analysis system 120 performs the analysis to compare the spectroscopy data with predetermined results that are desired, as shown at block 530.

If the spectroscopy data matches the desired predetermined results, the analysis system 120 makes no changes to the probe 110, and the method continues as described above. If the spectroscopy data does not match the predetermined results, the analysis system 120 determines updated parameter configuration(s) for the light sources of the probe 110 using machine learning algorithms, as shown at block 540. In one or more examples, the analysis system 120 uses APIs to access machine learning services to execute one or more machine learning algorithms, such as regression based, instance based, ANN based, or any other machine learning algorithm to determine updated parameter configurations for the light sources 310.

Further, the method includes sending the updated parameter configurations to the probe 110, as shown at block 550. The probe 110 updates the light sources 310 accordingly, thus resulting in different light waves being emitted in turn resulting in updated spectroscopy data captured by the sensors 330. The different light waves interact differently with the cells/neurons 320 in the tissue 350 of the patient 105, and thus optimizes the optogenetics treatment.

The technical solutions described herein thus address the technical challenges of optogenetics treatments, and address such technical challenges by embedding a probe equipped with low power light sources, such as LEDs, into a patient body. The probe is further equipped with a controller that can adjust the parameters of the light sources to adjust the light waves generated and/or emitted, thus adjusting the treatment of the cells and/or neurons of the patient. In one or more examples, changing the light waves changes the interaction of the chemical and/or protein concentrations in the cells.

In one or more examples, the controller adjusts the settings of the light sources using feedback from an analysis system that is external to the probe. The probe communicates with the analysis system using low power communication such as short range communication protocols like RF, NFC, and so on. The probe sends the spectroscopy resulting from the emitted light waves and captured by the sensors in the probe to the analysis system. The analysis system uses machine learning to determine updated parameters (or settings) for the light sources based on a comparison of the spectroscopy data with predetermined desired results. The analysis system sends the updated parameters to the probe, which is thus facilitate to change the light waves and optimize the optogenetics treatment. In one or more examples, the analysis system may be a computing device that is portable, such as a smartphone.

Thus, the technical solutions described herein facilitate a portable optogenetics treatment that is configurable and optimizable without inconveniencing the patient, who does not have to plug the embedded probe to the analysis system because the communication between the probe and the analysis system can be wireless. Further, with the probe being embedded within the patient's body, the patient does not have to be conscious, for example about his/her appearance.

The present technical solutions may be a system, a method, and/or a computer program product at any possible technical detail level of integration. The computer program product may include a computer readable storage medium (or media) having computer readable program instructions thereon for causing a processor to carry out aspects of the present technical solutions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technical solutions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present technical solutions.

Aspects of the present technical solutions are described herein with reference to flowchart illustrations and/or block diagrams of methods, apparatus (systems), and computer program products according to embodiments of the technical solutions. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present technical solutions. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are to be construed in the broadest sense, superseding any other implied definitions hereinbefore or hereinafter unless expressly asserted to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

It will also be appreciated that any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Such computer storage media may be part of the device or accessible or connectable thereto. Any application or module herein described may be implemented using computer readable/executable instructions that may be stored or otherwise held by such computer readable media.

The descriptions of the various embodiments of the technical features herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for implementing an optogenetics treatment using a probe and probe controller, wherein the probe controller is configured to control the probe to perform the method comprising:

emitting, by a light source arranged on the probe and in the direction of a sensor arranged on the probe, wherein the probe is embeddable in a tissue, a light wave to interact with a corresponding chemical in one or more cells in the tissue located inward from the light source and the sensor;

capturing, by the sensor arranged on the probe, a spectroscopy of the light wave interacting with the corresponding chemical, wherein the sensor comprises a surface enhanced Raman sensor;

storing, by a processor arranged on the probe, the spectroscopy based at least in part on the probe and a remote machine learning system being separated by a distance greater than a predetermined distance;

transmitting, by the sensor and in response to the probe and the remote machine learning system being separated by a distance less than the predetermined distance, the spectroscopy to the remote machine learning system;

receiving, by the probe, adjusted parameters for the light source based on the spectroscopy, wherein the adjusted parameters are determined by the remote machine learning system by comparing the spectroscopy to predetermined results of desired effects and to predetermined parameters for the probe; and adjusting, by a controller arranged on the probe, settings of the light source according to the received adjusted parameters to emit a different light wave to interact with the corresponding chemical.

2. The computer-implemented method of claim 1, wherein the light source comprises a plurality of light sources, and one or more of the light sources is configured to emit corresponding light waves associated with a respective chemical.

3. The computer-implemented method of claim 1, wherein the light source of the probe comprises a light emitting diode.

4. The computer-implemented method of claim 1, wherein adjusting the settings of the light source comprises adjusting a pulse width of the light wave.

5. The computer-implemented method of claim 1, wherein adjusting the settings of the light source comprises adjusting a pulse repetition frequency of the light wave.

6. The computer-implemented method of claim 1, wherein adjusting the settings of the light source comprises adjusting a time at which the light wave is emitted.

7. The computer-implemented method of claim 1, wherein adjusting the settings of the light source comprises adjusting a number of pulses emitted in the light wave.

8. A system comprising:
a probe configured to perform optogenetics treatment, the probe comprising:
  a light source;
  a sensor; and
  a controller; and
  a machine learning system configured to wirelessly communicate with the probe, wherein the system is configured to automatically optimize the optogenetics treatment, the automatic optimization comprising:
    emitting, by the light source of the probe and in the direction of the sensor, a light wave to interact with a corresponding chemical in one or more cells in a tissue located inward from the light source and the sensor, wherein the probe is embeddable in the tissue, and wherein the sensor is arranged on the probe;
    capturing, by the sensor of the probe, a spectroscopy of the light wave interacting with the corresponding chemical, wherein the sensor comprises a surface enhanced Raman sensor;
    storing, by a processor of the probe, the spectroscopy based at least in part on the probe and the machine learning system being separated by a distance greater than a predetermined distance;
    transmitting, by the sensor and in response to the probe and the machine learning system being separated by a distance less than the predetermined distance, the spectroscopy to the machine learning system;
    receiving, by the probe, from the machine learning system, adjusted parameters for the light source wherein the adjusted parameters are determined by the remote machine learning system by comparing the spectroscopy to predetermined results of desired effects and to predetermined parameters for the probe; and
    adjusting, by the controller of the probe, settings of the light source according to the received adjusted parameters to emit a different light wave to interact with the corresponding chemical.

9. The system of claim 8, wherein the light source comprises a plurality of light sources, each light source configured to emit corresponding light waves associated with a respective chemical.

10. The system of claim 8, wherein the light source of the probe is a light emitting diode.

11. The system of claim 8, wherein adjusting the settings of the light source comprises adjusting a pulse width of the light wave.

12. The system of claim 8, wherein adjusting the settings of the light source comprises adjusting a pulse repetition frequency of the light wave.

13. The system of claim 8, wherein adjusting the settings of the light source comprises adjusting a time at which the light wave is emitted.

14. The system of claim 8, wherein adjusting the settings of the light source comprises adjusting a number of pulses emitted in the light wave.

15. A computer program product comprising a non-transitory computer readable storage medium having program instructions embodied therewith, the program instructions executable by a processing circuit to cause the processing circuit to automatically optimize an optogenetics treatment, the automatic optimization comprising:
emitting, by a light source arranged on a probe and in the direction of a sensor arranged on the probe, a light wave to interact with a corresponding chemical in one or more cells in the a tissue located inward from the light source and the sensor, wherein the probe is embeddable in a tissue;

capturing, by the sensor of the probe, a spectroscopy of the light wave interacting with the corresponding chemical, wherein the sensor comprises a surface enhanced Raman sensor;

storing, by a processor arranged on the probe, the spectroscopy based at least in part on the probe and a remote machine learning system being separated by a distance greater than a predetermined distance;

transmitting, by the sensor and in response to the probe and the remote machine learning system being separated by a distance less than the predetermined distance, the spectroscopy to the remote machine learning system;

receiving, by the probe, from the machine learning system, adjusted parameters for the light source wherein the adjusted parameters are determined by the remote machine learning system by comparing the spectroscopy to predetermined results of desired effects and to predetermined parameters for the probe; and adjusting, by a controller of the probe, settings of the light source according to the received adjusted parameters to emit a different light wave to interact with the corresponding chemical.

16. The computer program product of claim 15, wherein the light source comprises a plurality of light sources, each light source configured to emit corresponding light waves associated with a respective chemical.

17. The computer program product of claim 15, wherein adjusting the settings of the light source comprises adjusting a pulse width of the light wave.

18. The computer program product of claim 15, wherein adjusting the settings of the light source comprises adjusting a pulse repetition frequency of the light wave.

19. A probe that is embeddable in a patient, the probe configured to perform an optogenetics treatment for the patient, the probe comprising:

a light source arranged on the probe and configured to emit a light wave to interact with a corresponding chemical in one or more cells in a tissue wherein the probe is embeddable in the tissue; and a sensor configured to capture a spectroscopy of the light wave interacting with the corresponding chemical, wherein the light source is configured to emit the light wave in the direction of the sensor, and wherein the one or more cells are located inward from the light source and the sensor, wherein the sensor comprises a surface enhanced Raman sensor; and a controller configured to:
store the spectroscopy based at least in part on the probe and a remote machine learning system being separated by a distance greater than a predetermined distance;

transmit, in response to the probe and a machine learning system being separated by a distance less than the predetermined distance, the spectroscopy to the remote machine learning system;

receive, in response, from the machine learning system, adjusted parameters for the light source wherein the adjusted parameters are determined by the remote machine learning system by comparing the spectroscopy to predetermined results of desired effects and to predetermined parameters for the probe; and adjust settings of the light source according to the received adjusted parameters to emit a different light wave to interact with the corresponding chemical.

20. The probe of claim 19, wherein the light source comprises a plurality of light sources, each light source configured to emit corresponding light waves associated with a respective chemical, and the sensor comprises a plurality of sensors, each sensor associated with a respective light source.

21. An analysis system configured to automatically adjust an optogenetics treatment for a patient, the analysis system comprising:

a memory; and a processor coupled with the memory, the processor configured to:

receive captured spectroscopy sent wirelessly by a probe that is embeddable within the patient, the spectroscopy captured by a light sensor of the probe in response to emission of a light wave by a light source of the probe, the light wave being emitted to activate one or more cells of the patient, wherein the spectroscopy is transmitted by the probe based at least in part on the probe and the analysis system being separated by a distance less than a predetermined distance, wherein the light sensor comprises a surface enhanced Raman sensor;

compare the captured spectroscopy with a predetermined spectroscopy;

determine an updated set of parameters for the light source of the probe in response to the captured spectroscopy not matching the predetermined spectroscopy wherein the updated parameters are determined by a machine learning algorithm by comparing the spectroscopy to predetermined results of desired effects and to predetermined parameters for the probe; and send the updated set of parameters to the probe to cause the light sensor to generate a different emission to activate the cells.

22. The analysis system of claim 21, wherein the light source comprises a plurality of light sources, each light source configured to emit corresponding light waves associated with a respective chemical, and the sensor comprises a plurality of sensors, each sensor associated with a respective light source.

23. The analysis system of claim 21, wherein adjusting the settings of the light source comprises adjusting at least one parameter from a group of parameters consisting of a pulse width of the light wave, a pulse repetition frequency of the light wave, a time at which the light wave is emitted, and a number of pulses emitted in the light wave.

\* \* \* \* \*